United States Patent [19]
Cesa et al.

[11] Patent Number: 5,034,560
[45] Date of Patent: Jul. 23, 1991

[54] SYNTHESIS OF ETHYLAMINES

[75] Inventors: Mark C. Cesa, South Euclid; Robert A. Dubbert, Solon, both of Ohio

[73] Assignee: The Standard Oil Company, Cleveland, Ohio

[21] Appl. No.: 599,944

[22] Filed: Oct. 19, 1990

[51] Int. Cl.$^5$ .................................... C07C 209/48
[52] U.S. Cl. .................................... 564/493; 564/490
[58] Field of Search ............................. 564/493

[56] References Cited

U.S. PATENT DOCUMENTS 3,574,754 4/1971 Specken .......................... 564/493
4,235,821 11/1980 Butte, Jr. et al. ................ 564/493
4,739,120 4/1988 Zuckerman .................... 564/493

FOREIGN PATENT DOCUMENTS 50-47910 4/1975 Japan .................................... 564/493
53-50109 5/1978 Japan .................................... 564/493

Primary Examiner—Richard L. Raymond
Assistant Examiner—Susan P. Treanor
Attorney, Agent, or Firm—C. S. Lynch; D. J. Untener; L. W. Evans

[57] ABSTRACT

Disclosed is a process for making ethylamines by the hydrogenation in a reaction zone of acetonitrile contained in a basic aqueous solution which also contains HCN, which comprises continuously passing hydrogen gas in contact with a flowing stream containing acetonitrile, water and HCN, which stream is in contact with a solid hydrogenation catalyst, wherein the hydrogen contact time is in the range from 0.5 seconds to 20 minutes and the molar ratio of $H_2$ to acetonitrile charged to said reaction zone is in the range 2–200:1.

8 Claims, No Drawings

SYNTHESIS OF ETHYLAMINES

This invention relates to the synthesis of ethylamines by the hydrogenation of impure or crude acetonitrile containing water and HCN.

It has been attempted to hydrogenate aqueous acetonitrile containing HCN in a batch reaction in an autoclave. See Japanese Kokai 1978/50,109, where it is noted that the alkalinity of the reaction mixture caused by the formation of the ethylamines during hydrogenation results in polymerization of the HCN, and that the polymers formed are adsorbed onto the catalyst surface, sharply reducing the catalytic activity.

The solution by the Japanese inventors, allowing the hydrogenation reaction of such an HCN-containing acetonitrile substrate was to keep the reaction mixture acidic throughout the course of the reaction by the addition of an organic acid while the hydrogenation is carried out. This is said to prevent the polymerization of the HCN, thus avoiding the deactivation of the catalyst used. However, the large amount of organic acid required is an obvious expense, making the process relatively commercially unattractive. Japanese Kokai 1975/47,910 solves the problems caused by the presence of HCN in the batch hydrogenation of such an acetonitrile substrate by simply removing the HCN from the aqueous acetonitrile prior to the hydrogenation reaction. This expedient is also expensive.

It is an object of the present invention to provide a process for making ethylamines by the hydrogenation of an impure aqueous acetonitrile composition containing HCN which is basic during the reaction.

Another object is to provide such a process which avoids polymerization of HCN during such reaction, with the consequent fouling of the catalyst.

Other objects, as well as aspects and advantages, of the invention will become apparent from a study of the specification including the specific examples and the claims.

These objects are realized by the present invention according to which there is provided a process for making ethylamines by the hydrogenation in a reaction zone of acetonitrile contained in a basic aqueous solution which also contains HCN, which comprises continuously passing hydrogen gas in contact with a flowing stream containing acetonitrile, water and HCN, which stream is in contact with a solid hydrogenation catalyst, wherein the hydrogen contact time is in the range from 0.5 seconds to 20 minutes and the molar ratio of $H_2$ to acetonitrile charged to said reaction zone is in the range 2-200:1. This ratio usually does not exceed 50:1, nor is it usually less than 5:1.

In contrast to the prior art discussed above, the continuous hydrogenation process of the present invention results in essentially no HCN polymerization and thus catalyst fouling with polymers.

The reaction temperature of our process is usually in the range 20° C.–300° C., most often 50° C.–200° C. The optimum contact time is lower at higher temperatures and at higher ratios of hydrogen gas to acetonitrile.

To obtain practical, economic rates of reaction, the present reaction requires a hydrogenation catalyst. Any of the solid hydrogenation catalysts can be used, such as those based on nickel, cobalt, iron, ruthenium, palladium, or rhodium and their compounds and complexes, including mixtures. Also applicable are the so-called Raney catalysts of nickel, cobalt and copper. Especially useful catalysts are: (1) catalysts based on nickel, including nickel catalysts promoted by one or more of aluminum, titanium, chromium, boron, iron, cobalt, zirconium, copper, zinc, palladium, and platinum; and (2) catalysts based on cobalt, including cobalt catalysts promoted with one or more of aluminum, manganese, silver, copper, chromium, nickel, zinc, calcium, and zirconium.

However, we regard our invention to be the reaction of aqueous acetonitrile containing HCN as an impurity in a continuous reaction made at the hydrogen contact times and hydrogen to acetonitrile ratios recited to be our invention, divorced from any designation of a specific solid catalyst.

Reaction pressure can range from atmospheric to 2000 psig or more. It is found that the most useful pressure range is from 50 to 1000 psig, particularly under conditions where the reactant crude acetonitrile is in the liquid phase. Thus, whether the acetonitrile reactant is in the liquid or vapor phase depends on the reaction conditions such as temperature and pressure, and our process can be effected in either event.

Our discovery of how to carry out the hydrogenation of basic aqueous acetonitrile containing HCN in a manner that avoids polymerization of HCN with consequent catalyst deactivation allows the use of a portion of the effluent from a propylene or propane ammoxidation reaction, from which most of the acrylonitrile product has preferably been removed, as the aqueous feed to our acetonitrile-to-ethylamines hydrogenation process. Even though our reaction mixture becomes basic as soon as ethylamines begin to form, the reaction when effected as set forth in the claims avoids HCN polymerization and the attendant problems. Such crude acetonitrile stream from the reaction of propylene or propane with ammonia and oxygen contains HCN as well as acetonitrile and water, and there is no necessity to remove HCN therefrom.

The acetonitrile stream fed to the hydrogenation reaction zone can contain acetonitrile in concentrations of 1 weight percent to 90 weight percent, or even more; water in concentrations of 0.1 to 90–95 weight percent; HCN concentrations up to 15 weight percent and usually at least 0.1 weight percent. The crude acetonitrile cut from the effluent of a propylene or propane ammoxidation reaction to produce acrylonitrile can contain other components such as acrylonitrile, methacrylonitrile, propionitrile, pyridine, methyl-substituted pyridines, oxazole, pyrazine, benzonitrile, cyanopyridine, cyanofurans, and methanol, as well as similar compounds, and these are present in the crude acetonitrile in varying amounts relative to one another, but the combined concentration of these components can rane from 0.1 to 25 weight percent of the crude acetonitrile, sufficient to account for the remaining mass of the crude acetonitrile after the acetonitrile, water and HCN are accounted for. Typical acetonitrile concentrations in the crude acetonitrile from the ammoxidation range from 25–85 weight percent; HCN from 0.1 to 6 or 7 weight percent; and water from 20–65 weight percent.

In the present process sulfur and halogen or their compounds are usually to be avoided in the reaction zone because of their deleterious effect on hydrogenation catalysts.

As is well known, ammonia when added to the reaction mixture in the hydrogenation of acetonitrile promotes the tendency to form more monoethylamine compared to di- and triethylamines than if not present.

In the present invention we can include ammonia (as a gas or in water solution) as part of the feed to the hydrogenation reaction zone for the same purpose when monoethylamine is the product most desired.

Moreover, it is within the scope of the invention to include an inert diluent gas such as nitrogen, either to help moderate the effect of exothermic heat produced, or to improve the flow of gases when relatively small amounts of hydrogen relative to acetonitrile and water are used.

The following examples are illustrative only. In these examples the hydrogen gas and the acetonitrile-containing streams were both fed downwardly through the tubular reactor containing the catalyst. The aqueous acetonitrile was in the liquid phase under the reaction conditions prevailing, except in Examples 6 and 7 the acetonitrile was in the vapor phase.

EXAMPLE 1

A stainless steel fixed-bed downward flow reactor of approximately 20 cc internal volume was charged with an intimate admixture of 12 cc of 20/30 mesh quartz chips and 8 cc (6.8497 g) of 20/30 mesh particles of a catalyst composed of 42 weight percent nickel supported on alumina with surface area 188 $m^2/g$, prepared by Calsicat Division of Mallinckrodt, Inc. Hydrogen was passed through the reactor at 500 psig with a flow rate of 228 mL/min (measured at ambient temperature and pressure) as the reactor was heated to 104.8° C. Then the following solutions were fed separately into the reactor as the hydrogen flow, pressure, and temperature were maintained as above: crude acetonitrile of approximate composition 52 weight percent acetonitrile, 42.3 weight percent water, 0.3 weight percent HCN, and also containing acetaldehyde, acetone, acrylonitrile, propionitrile, methanol, oxazole, butenenitriles, allyl alcohol, pyridine, and methyl pyridines at a flow rate of 4.46 g/hr; and concentrated aqueous ammonia solution at 6.46 g/hr. The feed mole ratios were as follows: $H_2:CH_3CN=10:1$; $NH_3:CH_3CN=1.95:1$. The hydrogen contact time was 55.5 sec. A sample of the product mixture was taken at 22.7 hours of reaction. Gas chromatographic analysis of the product sample showed that the conversion of acetonitrile was 99.3%. The product mixture contained monoethylamine, diethylamine, and triethylamine in mole ratio monoethylamine:diethylamine:triethylamine 94.0:6.1:0.048. The selectivity to ethylamines from acetonitrile was over 99%.

EXAMPLE 2

A stainless steel fixed-bed downward flow reactor of approximately 20 cc internal volume was charged with an intimate admixture of 12 cc of 20/30 mesh quartz chips and 3 cc (2.4189 g) of 20/30 mesh particles of a catalyst composed of 42 weight percent nickel supported on alumina with surface area 188 $m^2/g$, prepared by Calsicat Division of Mallinckrodt, Inc. Hydrogen was passed through the reactor at 500 psig with a flow rate of 451 mL/min (measured at ambient temperature and pressure) as the reactor was heated to 100° C. Then the following solutions were fed separately into the reactor as the hydrogen flow, pressure, and temperature were maintained as above: crude acetonitrile of approximate composition 52 weight percent acetonitrile, 42.3 weight percent water, 0.3 weight percent HCN, and also containing acetaldehyde, acetone, acrylonitrile, propionitrile, methanol, oxazole, butenenitriles, allyl alcohol, pyridine, and methyl pyridines at a flow rate of 4.94 g/hr; and concentrated aqueous ammonia solution at 7.0 g/hr. The feed mole ratios were as follows: $H_2:CH_3CN=20.6:1$; $NH_3:CH_3=2.2:1$. The hydrogen contact time was 10.7 sec. A sample of the product mixture was taken after 17 hours of reaction. Gas chromatographic analysis of the product sample showed that the conversion of acetonitrile was 96.5%. The product mixture contained monoethylamine, diethylamine, and N-ethylidene ethylamine in the mole ratios monoethylamine:diethylamine:N-ethylidene ethylamine 97.4:2.0:0.33. The selectivity to ethylamines from acetonitrile was over 99%.

EXAMPLE 3

A stainless steel fixed-bed downward flow reactor of approximately 20 cc internal volume was charged with 3.2 cc (2.5076 g) of 20/30 mesh particles of a catalyst composed of 42 weight percent nickel supported on alumina with surface area 188 $m^2/g$, prepared by Calsicat Division of Mallinckrodt, Inc. Hydrogen was passed through the reactor at 500 psig with a flow rate of 773 ml/min (measured at ambient temperature and pressure) as the reactor was heated to 100° C. Then the following solutions were fed separately into the reactor as the hydrogen flow, pressure, and temperature were maintained as above: crude acetonitrile of approximate composition 52 weight percent acetonitrile, 42.35 weight percent water, 0.3 weight percent HCN, and also containing acetaldehyde, acetone, acrylonitrile, propionitrile, methanol, oxazole, butenenitriles, allyl alcohol, pyridine, and methyl pyridines at a flow rate of 5.46 g/hr; and concentrated aqueous ammonia solution at 7.61 g/hr. The feed mole ratios were as follows: $H_2:CH_3CN=29:1$; $NH_3:CH_3CN=1.96:1$. The hydrogen contact time was 6.3 sec. A sample of the product mixture was taken after 17.5 hours of reaction. Gas chromatographic analysis of the product sample showed that the conversion of acetonitrile was 96.8%. The product mixture contained monoethylamine, diethylamine, and N-ethylidene ethylamine in mole ratio monoeihylamine:diethylamine:N-ethylidene ethylamine 97.8:1.77:0.41. The selectivity to ethylamines from acetonitrile was 90.5%.

EXAMPLE 4

A stainless steel fixed-bed downward flow reactor of approximately 20 cc internal volume was charged with an intimate admixture of 8 cc of 20/30 mesh quartz chips and 2 cc (1.5922 g) of 20/30 mesh particles of a catalyst composed of 42 weight percent nickel supported on alumina with surface area 188 $m^2/g$, prepared by Calsicat Division of Mallinckrodt, Inc. Hydrogen was passed through the reactor at 500 psig with a flow rate of 234 mL/min (measured at ambient temperature and pressure) as the reactor was heated to 107° C. Then crude acetonitrile of approximate composition 52 weight percent acetonitrile, 42.3 weight percent water, 0.3 weight percent HCN, and also containing acetaldehyde, acetone, acrylonitrile, propionitrile, methanol, oxazole, butenenitriles, allyl alcohol, pyridine, and methyl pyridines was fed into the reactor at a :low rate of 4.44 g/hr as the hydrogen flow, pressure, and temperature were maintained as above. The mole ratio $H_2:CH_3CN=11.9:1$. The hydrogen contact time was 13.5 sec. A sample of the product mixture was taken after 19.75 hours of reaction. Gas chromatographic analysis of the product sample showed that the conversion o: acetonitrile was 73.2%. The product mixture contained monoethylamine, diethylamine, triethylamine, and N-ethylidene ethylamine in mole ratio monoethylamine:diethylamine:triethylamine:N-ethylidene ethylamine 61.1:21.9:1.9:15.1. The yield and selectivity to ethylamines from acetonitrile were 53.3% and 71.4%, respectively.

COMPARATIVE EXAMPLE A 51.26 g of crude acetonitrile of approximate composition 52 weight percent acetonitrile, 42.3 weight percent water, 0.3 weight percent HCN, and the remainder acetaldehyde, acetone, acrylonitrile, propionitrile, methanol, oxazole, butenenitriles, allyl alcohol, pyridine, and methyl pyridines was placed under an argon atmosphere in a stirred stainless steel autoclave reactor of 300 cc volume. 3.44 g (4.6 cc) of a catalyst composed of 42 weight percent nickel supported on alumina, with surface area 188 m$^2$/g, prepared by Calsicat Division of Mallinckrodt, Inc., was added to the reactor. The reactor was sealed and pressurized to 500 psig with hydrogen. The reaction mixture was stirred under 500 psig of hydrogen at 129.5° C. for 3.5 hours, and hydrogen was continually added to the reactor to maintain the hydrogen pressure at 500 psig. After this time the reactor was cooled and opened, and the contents were analyzed by gas chromatography. The analysis revealed that the acetonitrile conversion was 99.7%, and a mixture of monoethylamine, N-ethylidene ethylamine, and diethylamine was formed in 44.4% yield and 44.5% selectivity, respectively, with a mole ratio of monoethylamine:diethylamine:N-ethylidene ethylamine of 92.1:7.9:trace. The gas chromatogram of the product mixture showed large amounts of material of high molecular weight.

EXAMPLE 5

A stainless steel fixed-bed downward flow reactor of approximately 20 cc internal volume was charged with an intimate admixture of 3 cc of 20/30 mesh quartz chips and 2 cc (1.4256 g) of 20/30 mesh particles of a catalyst composed of 52 weight percent nickel supported on silica/alumina (SiO$_2$:Al$_2$O$_3$=2.8:1 by weight) with approximate surface area 300 m$^2$/g, prepared by United Catalysts, Inc. Hydrogen was passed through the reactor at 500 psig with a flow rate of 255 mL/min (measured at ambient temperature and pressure) as the reactor was heated to 105° C. Then crude acetonitrile of approximate composition 57.4 weight percent acetonitrile, 37.8 weight percent water, 0.6 weight percent HCN, and also containing acetaldehyde, acetone, acrylonitrile, propionitrile, methanol, oxazole, butenenitriles, allyl alcohol, pyridine, and methyl pyridines was fed into the reactor at a flow rate of 3.85 g/hr as the hydrogen flow, pressure, and temperatures were maintained as above. The mole ratio H$_2$:CH$_3$CN=13.0:1. The hydrogen contact time was 12.4 sec A sample of the product mixture was taken after 21.33 hours of reaction. Gas chromatographic analysis of the product sample showed that the conversion of acetonitrile was 99.4%. The product mixture contained monoethylamine, diethylamine, and triethylamine in mole ratio monoethylamine:diethylamine:triethylamine 88.7:11.1:0.2. The selectivity to ethylamines from acetonitrile was over 99%.

EXAMPLE 6

A stainless steel fixed-bed downward flow reactor of approximately 20 cc internal volume was charged with an intimate admixture of 3 cc of 30/40 mesh quartz chips and 2 cc (1.4088 g) of 20/30 mesh particles of a catalyst composed of 52 weight percent nickel supported on silica/alumina (SiO$_2$:Al$_2$O$_3$=2.8:1 by weight) with approximate surface area 300 m$^2$/g, prepared by United Catalysts, Inc. Hydrogen was passed through the reactor at 500 psig with a flow rate of 273 mL/min (measured at ambient temperature and pressure) as the reactor was heated to 180° C. Then the following solutions were fed separately into the reactor as the hydrogen flow, pressure, and temperature were maintained as above: crude acetonitrile of approximate composition 57.4 weight percent acetonitrile, 37.8 weight percent water, 0.6 weight percent HCN, and also containing acetaldehyde, acetone, acrylonitrile, propionitrile, methanol, oxazole, butenenitriles, allyl alcohol, pyridine, and methyl pyridines at a flow rate of 4.12 g/hr; and concentrated aqueous ammonia solution at 6.17 g/hr. The feed mole ratios were as follows: H$_2$:CH$_3$CN=12.5:1; NH$_3$:CH$_3$CN=2.0:1. The hydrogen contact time was 9.7 sec. A sample of the product mixture was taken after 17 hours of reaction. Gas chromatographic analysis of the product sample showed that the conversion of acetonitrile was 99.9%. The product mixture contained monoethylamine, diethylamine, and triethylamine in mole ratio monoethylamine:diethylamine:triethylamine 89.8:9.6:0.6. The selectivity to ethylamines from acetonitrile was over 99%.

EXAMPLE 7

A stainless steel fixed-bed downward flow reactor of approximately 20 cc internal volume was charged with an intimate admixture of 3 cc of 30/40 mesh quartz chips and 2 cc (1.4088 g) of 20/30 mesh particles of a catalyst composed of 52 weight percent nickel supported on silica/alumina (SiO$_2$:Al$_2$O$_3$=2.8:1 by weight) with approximate surface area 300 m$^2$/g, prepared by United Catalysts, Inc. Hydrogen was passed through the reactor at 200 psig with a flow rate of 267 mL/min (measured at ambient temperature and pressure) as the reactor was heated to 100° C. Then the following solutions were fed separately into the reactor as the hydrogen flow, pressure, and temperature were maintained as above: crude acetonitrile of approximate composition 57.4 weight percent acetonitrile, 37.8 weight percent water, 0.6 weight percent HCN and also containing acetaldehyde, acetone, acrylonitrile, propionitrile, methanol, oxazole, butenenitriles, allyl alcohol, pyridine, and methyl pyridines at a flow rate of 4.12 g/hr; and concentrated aqueous ammonia solution at 6.17 g/hr. The feed mole ratios were as follows: H$_2$:CH$_3$CN=12.7:1; NH$_3$:CH$_3$CN=2.0:1. The hydrogen contact time was 4.8 sec. A sample of the product mixture was taken after 3 hours of reaction. Gas chromatographic analysis of the product sample showed that the conversion of acetonitrile was 45.3%. The product mixture contained monoethylamine, with no detectable diethylamine or triethylamine. The selectivity to monoethylamine from acetonitrile was over 99%.

EXAMPLE 8

A stainless steel fixed-bed downward flow reactor of approximately 20 cc internal volume was charged with an intimate admixture of 12 cc of 20/30 mesh quartz chips and 8 cc (6.2428 g) of 20/30 mesh particles of a catalyst composed of 52 weight percent nickel supported on silica/alumina (SiO$_2$:Al$_2$O$_3$=2.8:1 by weight)

with approximate surface area 300 m$^2$/g, prepared by United Catalysts, Inc. Hydrogen was passed through the reactor at 500 psig with a flow rate of 222.5 mL/min (measured at ambient temperature and pressure) as the reactor was heated to 100° C. Then the following solutions were fed separately into the reactor as the hydrogen flow, pressure, and temperature were maintained as above: crude acetonitrile of approximate composition 52 weight percent acetonitrile, 42.3 weight percent water, 0.3 weight percent HCN, and also containing acetaldehyde, acetone, acrylonitrile, propionitrile, methanol, oxazole, butenenitriles, allyl alcohol, pyridine, and methyl pyridines at a flow rate of 4.46 g/hr; and concentrated aqueous ammonia solution at 6.46 g/hr. The feed mole ratios were as follows: H$_2$:CH$_3$CN=10:1; NH$_3$:CH$_3$CN =2.1. The hydrogen contact time was 58 sec. Samples of the product mixture were taken at regular intervals over a 166 hour period. Gas chromatographic analysis of the product samples showed that the conversion of acetonitrile was maintained at an average 97.8% (range 92.3% - 100%). The product mixture contained monoethylamine, diethylamine, triethylamine, N-ethylidene ethylamine, and ethanol in mole ratio monoethylamine:diethylamine:-triethylamine:N-ethylidene ethylamine:ethanol 96.0:3.6:0.007:0.20:0.08. The selectivity to ethylamines from acetonitrile was maintained at an average 98.7%. This example shows that even over the long term the process of the present invention avoids fouling of the catalyst with polymers, with consequent deactivation thereof, in contrast to the teachings of the prior art. This is consistent with our microscopic examination of the catalyst, which showed no evidence of any polymer deposition or other fouling of the catalyst surface.

EXAMPLE 9

A stainless steel fixed-bed downward flow reactor of approximately 20 cc internal volume was charged with an intimate admixture of 3 cc of 30/40 mesh quartz chips and 2 cc (2.1320 g) of 20/30 mesh particles of a catalyst composed of 54 weight percent cobalt and 2.6% zirconium supported on kieselguhr, prepared by United Catalysts Inc. Hydrogen was passed through the reactor at 500 psig with a flow rate of 258 mL/min (measured at ambient temperature and pressure) as the reactor was heated to 100° C. Then the following solutions were fed separately into the reactor as the hydrogen flow, pressure and temperature were maintained as above: crude acetonitrile of approximate composition 57.4 weight percent acetonitrile, 37.8 weight percent water, 0.6 weight percent HCN, and also containing acetaldehyde acetone, acrylonitrile, propionitrile, methanol, oxazole, butenenitriles, allyl alcohol, pyridine, and methyl pyridines at a flow rate of 4.12 g/hr; and concentrated aqueous ammonia solution at 6.17 g/hr. The feed mole ratios were as follows: H$_2$:CH$_3$CN=12.2:1; NH$_3$:CH$_3$CN=2.0:1. The hydrogen contact time was 12.4 sec. A sample of the product mixture was taken after 3 hours of reaction. Gas chromatographic analysis of the product sample showed that the conversion of acetonitrile was 61.3%. The product mixture contained monoethylamine, diethylamine, and N-ethylidene ethylamine in mole ratio monoethylamine:diethylamine:N-ethylidene ethylamine 91.0:8 9:0.1. The selectivity to ethylamines from acetonitrile was over 99%.

As will be evident to those skilled in the art, various modifications of this invention can be made or followed in the light of the foregoing disclosure and discussion without departing from the spirit and scope of the disclosure or from the scope of the claims.

WHAT WE CLAIM IS:

1. A process for making ethylamines by the hydrogenation in a reaction zone of acetonitrile contained in a basic aqueous solution which also contains HCN, which comprises continuously passing hydrogen gas in contact with a flowing stream containing acetonitrile, water and HCN, which stream is in contact with a solid hydrogenation catalyst, wherein the hydrogen contact time is in the range from 0.5 seconds to 20 minutes and the molar ratio of H$_2$ to acetonitrile charged to said reaction zone is in the range 2-200:1.

2. A process of claim 1 wherein the molar ratio of H$_2$ to acetonitrile charged to said reaction zone is at least 5:1.

3. A process of claim 1 wherein the molar ratio of H$_2$ to acetonitrile charged to said reaction zone does not exceed 50:1.

4. A process of claim 2 wherein the molar ratio of H$_2$ to acetonitrile charged to said reaction zone does not exceed 50:1.

5. A process of claim 1 wherein ammonia is also charged to said reaction zone.

6. A process of claim 1 wherein the pressure in said reaction zone is in the range from 50 to 1000 psig.

7. A process of claim 1 wherein the temperature in said reaction zone is in the range from 50° C.–175° C.

8. A process of claim 2 wherein the temperature in said reaction zone is in the range from 50° C.–175° C.

* * * * *